(12) United States Patent
An et al.

(10) Patent No.: US 12,144,978 B2
(45) Date of Patent: Nov. 19, 2024

(54) NEEDLE TIP MOUNTED ON SKIN CARE DEVICE AND SKIN CARE DEVICE

(71) Applicant: JEISYS MEDICAL INC., Seoul (KR)

(72) Inventors: Kyoung Ho An, Seoul (KR); Seung Eok Jeon, Incheon (KR)

(73) Assignee: Jeisys Medical Inc., Seoul (KR)

( * ) Notice: Subject to any disclaimer, the term of this patent is extended or adjusted under 35 U.S.C. 154(b) by 234 days.

(21) Appl. No.: 17/688,213

(22) Filed: Mar. 7, 2022

(65) Prior Publication Data

US 2022/0184381 A1 Jun. 16, 2022

Related U.S. Application Data

(63) Continuation of application No. 16/697,129, filed on Nov. 26, 2019, now Pat. No. 11,298,529, which is a continuation of application No. PCT/KR2019/006259, filed on May 24, 2019.

(30) Foreign Application Priority Data

May 25, 2018 (KR) .......................... 10-2018-0059595

(51) Int. Cl.
| | |
|---|---|
| *A61N 1/05* | (2006.01) |
| *A61B 18/14* | (2006.01) |
| *A61N 1/04* | (2006.01) |
| *A61N 1/32* | (2006.01) |

(52) U.S. Cl.
CPC ........... *A61N 1/0502* (2013.01); *A61N 1/322* (2013.01); *A61N 1/328* (2013.01); *A61B 2018/143* (2013.01); *A61N 1/0476* (2013.01)

(58) Field of Classification Search
None
See application file for complete search history.

(56) References Cited

U.S. PATENT DOCUMENTS

| | | |
|---|---|---|
| 7,824,394 B2 | 11/2010 | Manstein |
| 9,289,605 B2 | 3/2016 | Choi |
| 2005/0222565 A1 | 10/2005 | Manstein |

(Continued)

FOREIGN PATENT DOCUMENTS

| | | |
|---|---|---|
| KR | 10-2010-0096124 A | 9/2010 |
| KR | 10-1066883 B1 | 9/2011 |

(Continued)

OTHER PUBLICATIONS

International Search Report issued in PCT/KR2019/006259; mailed Aug. 19, 2019.

(Continued)

*Primary Examiner* — Michael W Kahelin
(74) *Attorney, Agent, or Firm* — Leydig, Voit & Mayer, Ltd.

(57) ABSTRACT

A needle tip mounted on a skin care device and the skin care device are provided to prevent a proximity effect. The needle tip includes a case, a holder disposed in the case and reciprocating in a vertical direction, and a plurality of needle electrodes disposed in the holder. A current is applied to the plurality of needle electrodes, and the plurality of needle electrodes include a first group of needle electrodes and a second group of needle electrodes, to which the current is applied at mutually different times.

19 Claims, 7 Drawing Sheets

First diagonal line

(56) References Cited

U.S. PATENT DOCUMENTS

| | | | |
|---|---|---|---|
| 2007/0142885 A1 | 6/2007 | Hantash et al. | |
| 2008/0082090 A1* | 4/2008 | Manstein | A61B 18/203 606/9 |
| 2009/0112205 A1* | 4/2009 | McGill | A61B 18/14 606/41 |
| 2012/0158100 A1* | 6/2012 | Schomacker | A61B 18/1477 607/101 |
| 2014/0194789 A1 | 7/2014 | Ko | |
| 2016/0228178 A1* | 8/2016 | Lei | A61N 1/06 |
| 2021/0038881 A1 | 2/2021 | Hinman et al. | |

FOREIGN PATENT DOCUMENTS

| | | |
|---|---|---|
| KR | 10-2012-0140639 A | 12/2012 |
| KR | 10-2017-0014482 A | 2/2017 |

OTHER PUBLICATIONS

An Office Action mailed by the Korean Intellectual Property Office on Apr. 1, 2021, which corresponds to Korean Patent Application 10-2021-0001916 and is related to U.S. Appl. No. 16/697,129.

* cited by examiner

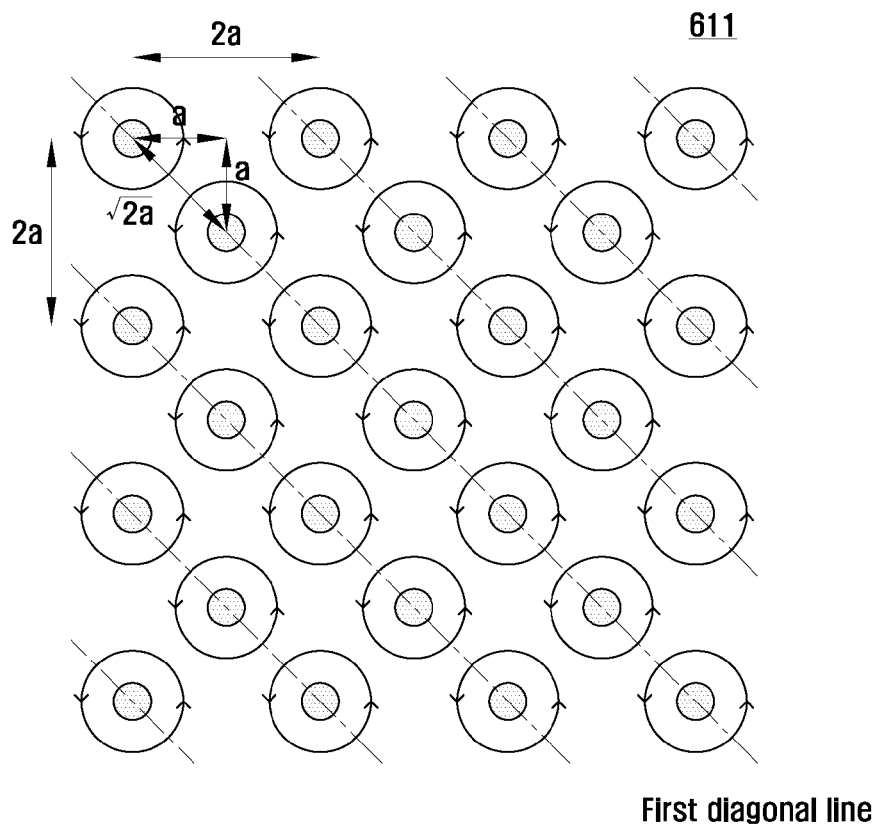
First diagonal line
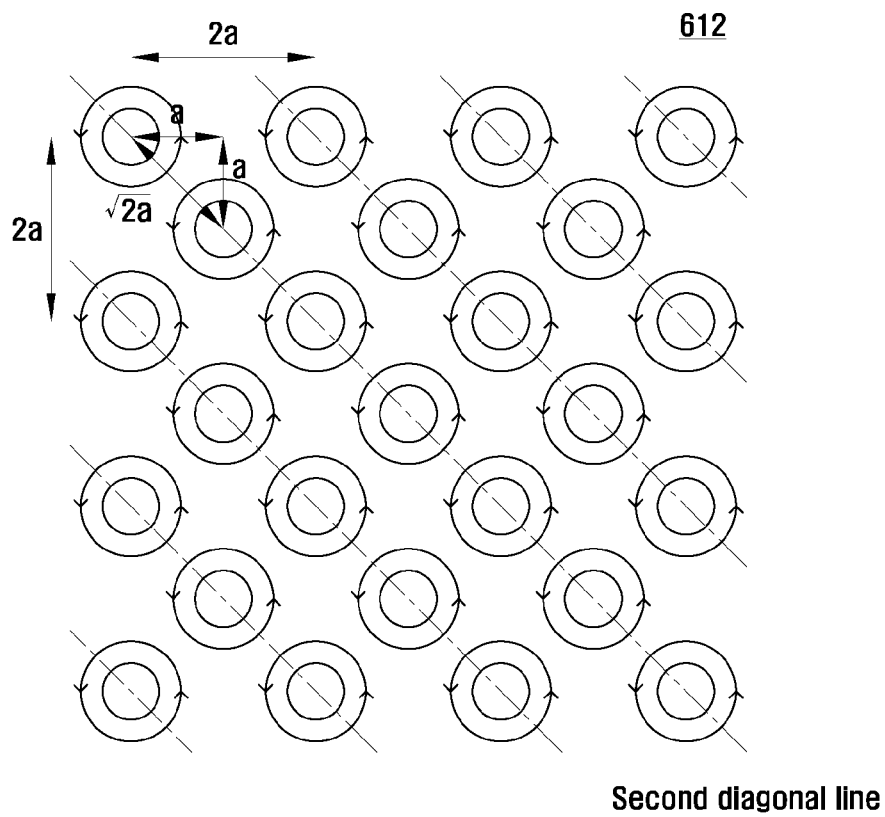
Second diagonal line

NEEDLE TIP MOUNTED ON SKIN CARE DEVICE AND SKIN CARE DEVICE

CROSS-REFERENCE TO RELATED APPLICATIONS

The present application is a continuation application of U.S. patent application Ser. No. 16/697,129, filed on Nov. 26, 2019, (now U.S. Pat. No. 11,298,529) which is a continuation of International Patent Application No. PCT/KR2019/006259, filed May 24, 2019, which is based upon and claims the benefit of priority to Korean Patent Application No. 10-2018-0059595, filed on May 25, 2018. The disclosures of the above-listed applications are hereby incorporated by reference herein in their entirety.

BACKGROUND

Embodiments of the inventive concept described herein relates to a needle tip mounted on a skin care device, capable of preventing a proximity effect made due to alternating oscillation, and a skin care device.

Recently, a skin care device has been developed to remove winkles, recover skin elasticity, and remove sebum. This is because a wrinkle-free, taut skin, thick, dense, non-sagging skin allows a person to look younger and contributes to an attractive appearance of the person.

There are several types of skin care devices such as an high-intensity focused ultrasound (HIFU)-type skin care device to oscillate an ultrasound, a radio frequency (RF) type skin care device to oscillate a high frequency, and an optical-type device to irradiate a laser beam.

According to the type of oscillating a high frequency, a single needle electrode or a plurality of needle electrodes are invaded into a deep portion (for example, a derma layer) of a skin at a target point (for example, a face) and a current is applied to the deep portion of the skin at the target point. Accordingly, as the high frequency is oscillated in the deep portion of the skin, damaged collagen and elastic fibers are removed, and new collagen and elastic fibers may be formed, due to thermal energy generated from the high-frequency oscillation. Furthermore, the high-frequency oscillation at the deep portion of the skin is effective in improving pigmentation of the skin, acne marks and wrinkles.

In this case, when a cutting edge of an end portion of a single or a plurality of RF needle electrodes is exposed and remaining portions of the RF needle electrodes are coated with an insulating material, a high frequency may be intensively transmitted to the deep portion of the skin (see FIGS. 1A and 1B; FIG. 1A illustrates the case that a needle electrode is not coated with an insulating material, and FIG. 1B illustrates the case that a needle electrode is coated with an insulating material).

Skin care devices to oscillate a high frequency are classified into a bipolar type in which a plurality of needle electrodes have two polarities, and a mono polar type in which a plurality of needle electrodes have one polarity and a ground electrode is provided separately).

In the bipolar type, the current applied to the needle electrode having the first polarity is refluxed to the needle electrode having the second polarity. Therefore, the high frequency oscillates between the plurality of needle electrodes, so the high frequency can be applied intensively to the local range.

In the mono polar type, the current applied to the needle electrode is refluxed to the ground electrode disposed at the non-target point (for example, the patient's belly). Therefore, since the high frequency oscillates over a wide range, the high frequency may be applied to the vicinity of the target point.

In the mono polar type, when a plurality of needle electrodes have to be disposed to be close to each other, a high frequency may be oscillated at the appropriate density in the deep portion of the skin at the target point.

In this case, when a current is applied to the adjacent needle electrodes in the same direction, the magnetic field generated from each of the plurality of needle electrodes is cancelled (Magnetic field cancellation) between the adjacent needle electrodes and is not cancelled at an outer portion of the adjacent needle electrode according to the right handed screw rule of the adjacent needle electrodes.

Therefore, as each of the adjacent needle electrode is closer to a needle electrode at the counterpart, a lower density current flows, and as the needle electrode is farther away from the needle electrode at the counter part, a higher density current flows. In other words, a deflected current flows through one conductive line, and even the distribution of the high-frequency energy oscillated from the deflected current is deflected (see FIG. 2).

In addition, to the contrary, when a current is applied to the adjacent needle electrodes in the opposite directions, as each of adjacent needle electrodes is closer to a needle electrode at the counterpart, a higher density current flows, and as each of the adjacent needle electrodes is father away from the needle electrode at the counterpart, a lower density current flows.

In other words, even if currents are applied in different directions to adjacent needle electrodes, a deflected current flows through a conductive line, so even the distribution of the high frequency energy oscillated by the current is deflected, which is similar to the case that the current is applied in the same direction.

Regarding the expanded interpretation of this phenomenon, when a plurality of needle electrodes are arranged in the form of a matrix and a current is applied in the same direction, the most part of magnetic fields are cancelled between needle electrodes disposed at the center of the matrix (see 33 in FIG. 3), and the least part of magnetic fields are cancelled between needle electrodes disposed at the border of the matrix (see 31 in FIG. 3). Meanwhile, the magnetic fields of needle electrodes between the center and the border of the matrix are cancelled to the intermediate cancellation extent between the cancellation extent at the center and the cancellation extent at the border (see 32 in FIG. 3).

Thus, the current flows while being deflected to the needle electrode disposed at the border of the matrix, so even the high frequency energy is deflected to the border. Furthermore, when a current is applied to the plurality of needle electrodes in different directions, the high frequency energy is deflected toward the center of the plurality of needle electrodes.

The above phenomenon is referred to as a proximity effect. Meanwhile, the epidermis effect is a kind of proximity effect, and refers to a phenomenon in which high frequency energy is deflected in one needle electrode.

In general, in the procedure of the monopolar type, a proximity effect occurs, so the high frequency energy is distributed while being deflected in the deep portion of the skin at the target point, which causes the skin improvement effect to be lowered.

SUMMARY

Embodiments of the inventive concept provide a needle tip mounted on a skin care device, capable of preventing a proximity effect, and a skin care device.

The objects of the inventive concept are not limited to the above, but other effects, which are not mentioned, will be apparently understood to those skilled in the art.

According to an exemplary embodiment, a needle tip mounted on a skin care device may include a case, a holder disposed in the case and reciprocating in a vertical direction, and a plurality of needle electrodes disposed in the holder, in which a current is applied to the plurality of needle electrodes. The plurality of needle electrodes may include a first group of needle electrodes and a second group of needle electrodes to which the current is applied at mutually different times.

The plurality of needle electrodes may be arranged in at least one of one or more rows and one or more columns on a plane perpendicular to the vertical direction, and the first group of needle electrodes and the second group of needle electrodes may be alternately arranged based on the one or more rows and alternately arranged based on the one or more column.

All the first group of the needle electrodes may be arranged on the plane perpendicular to the vertical direction in one or more first diagonal lines which are inclined with respect to the one or more rows or the one or more columns and mutually parallel to each other, all the second group of the needle electrodes may be arranged on the plane perpendicular to the vertical direction in one or more second diagonal lines which are inclined with respect to the one or more rows or the one or more columns and mutually parallel to each other, and the one or more first diagonal lines may be mutually parallel to the one or more second diagonal lines.

The one or more first diagonal lines and the one or more second diagonal lines may be arranged on the plane perpendicular to the vertical direction to be inclined at 45 degrees with respect to all the one or more rows and the one or more column.

The number of the plurality of needle electrodes may be 49, the number of the one or more rows may be seven, and the number of the one or more columns may be seven.

An alternating current may be applied to the plurality of needle electrodes.

The current may be alternately applied to the first group of needle electrodes and the second group of needle electrodes in the plurality of needle electrodes.

The first group of needle electrodes and the second group of needle electrodes may be connected with the same power source in parallel.

The needle tip may be mounted on a skin care device in a monopolar scheme.

A skin care device may include a main body in which a display module and an operating module are disposed, a conductive module extending to one side of the main body and including a first cable and a second cable, a hand piece disposed on the first cable, a needle tip mounted on the hand piece, a driving module to drive the needle tip, a ground electrode pad disposed on the second cable, and an electronic control module electrically connected with the needle tip through the first cable and electrically connected with the ground electrode pad through the second cable. The needle tip may include a case, a holder disposed in the case to reciprocate in a vertical direction by the driving module, and a plurality of needle electrodes disposed in the holder. A current may be applied to the plurality of needle electrodes by the electronic control module, and the plurality of needle electrodes may include a first group of needle electrodes and a second group of needle electrodes to which the current is at mutually different times.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIGS. 7A and 7B is a plan view illustrating that a first group of needle electrodes and a second group of needle electrodes are divided, according to the inventive concept.

DETAILED DESCRIPTION

Figure 1A:
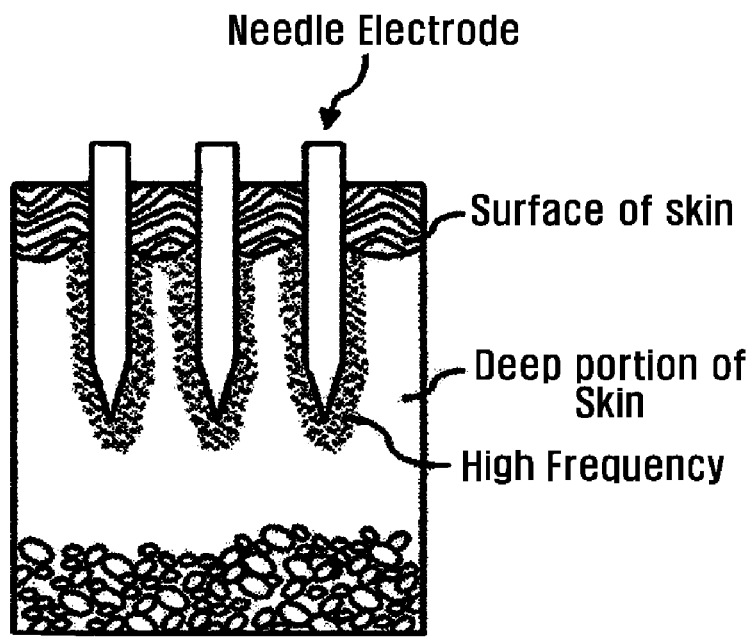
FIGS. 1A and 1B is a schematic view illustrating that a high frequency is applied using an RF needle electrode.

Advantage points and features of the prevent invention and a method of accomplishing thereof will become apparent from the following description with reference to the following figures, wherein embodiments will be described in detail with reference to the accompanying drawings. However, the inventive concept may be embodied in various different forms, and should not be construed as being limited only to the illustrated embodiments. Rather, these embodiments are provided as examples so that this inventive concept will be thorough and complete, and will fully convey the concept of the inventive concept to those skilled in the art. The inventive concept may be defined by scope of the claims.

The terminology used in the inventive concept is provided for the illustrative purpose, but the inventive concept is not limited thereto. As used herein, the singular terms "a," "an" and "the" are intended to include the plural forms as well, unless the context clearly indicates otherwise. Furthermore, it will be further understood that the terms "comprises", "comprising," "includes" and/or "including", when used herein, specify the presence of stated components, but do not preclude the presence or addition of one or more other components. The same reference numerals will be assigned to the same component throughout the whole specification, and "and/or" refers to that components described include not only individual components, but at least one combination of the components. It will be understood that, although the terms "first", "second", etc., may be used herein to describe various components, these components should not be limited by these terms. These terms are only used to distinguish one component from another component. Thus, a first component to be described below may be a second component without departing from the teachings of the inventive concept.

Unless otherwise defined, all terms (including technical and scientific terms) used herein have the same meaning as commonly understood by those skilled in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms, such as "below", "beneath", "lower", "above", "upper", and the like, may be used herein for ease of description to describe one component or feature's relationship to another component(s) or feature(s) as illustrated in accompanying drawings. It will be understood that the spatially relative terms are intended to encompass different orientations of the components in use or operation in addition to the orientation depicted in the drawings. For example, when a component illustrated in accompanying drawings is reversed, a component provided 'below' or 'beneath' another component may be placed 'above' another component. Accordingly, the term "below" may include both concepts of "below" and "above". A component may be oriented in a different direction. Accordingly, terminology having relatively spatial concepts may be variously interpreted depending on orientations.

Figure 4:
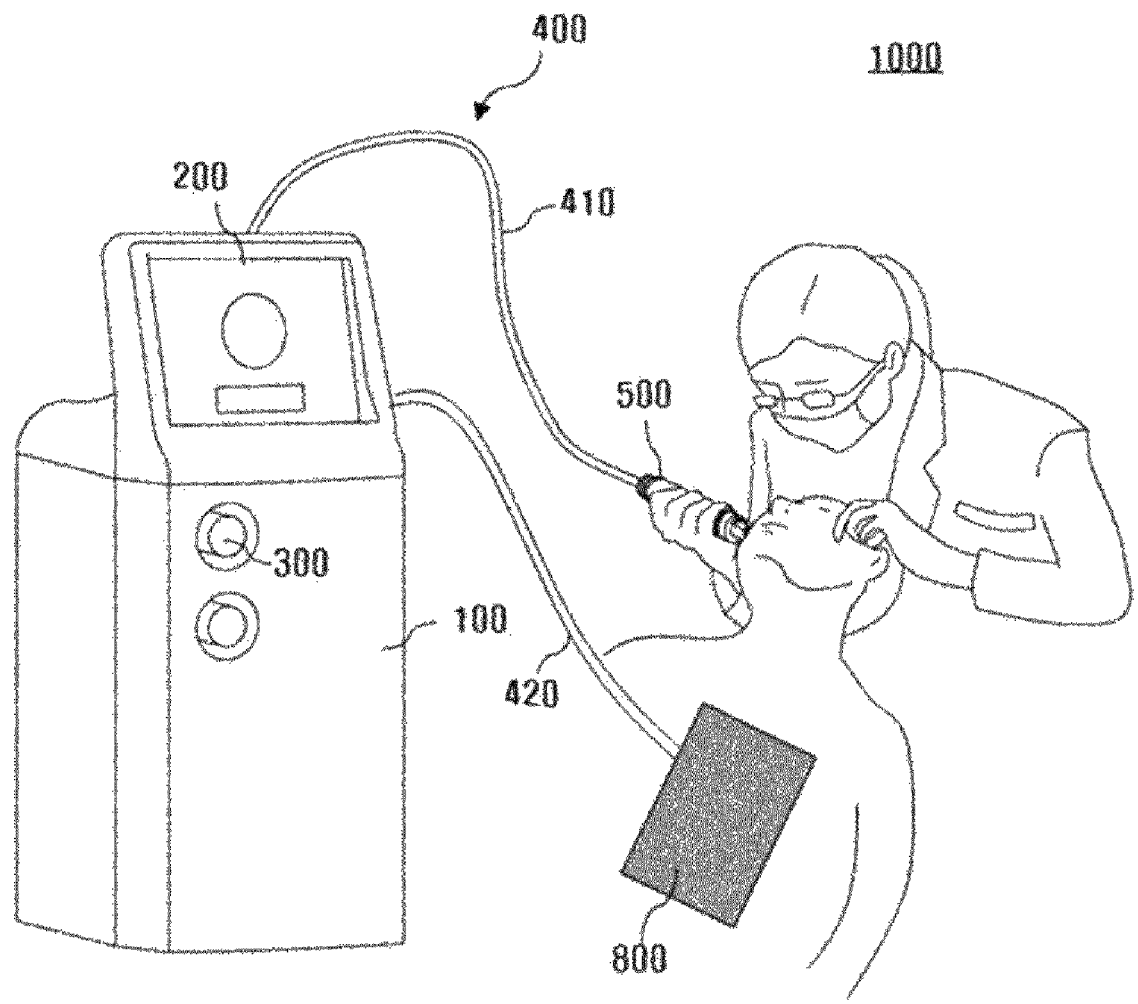
FIG. 4 is a schematic view illustrating a skin care device according to the inventive concept.
Figure 5:
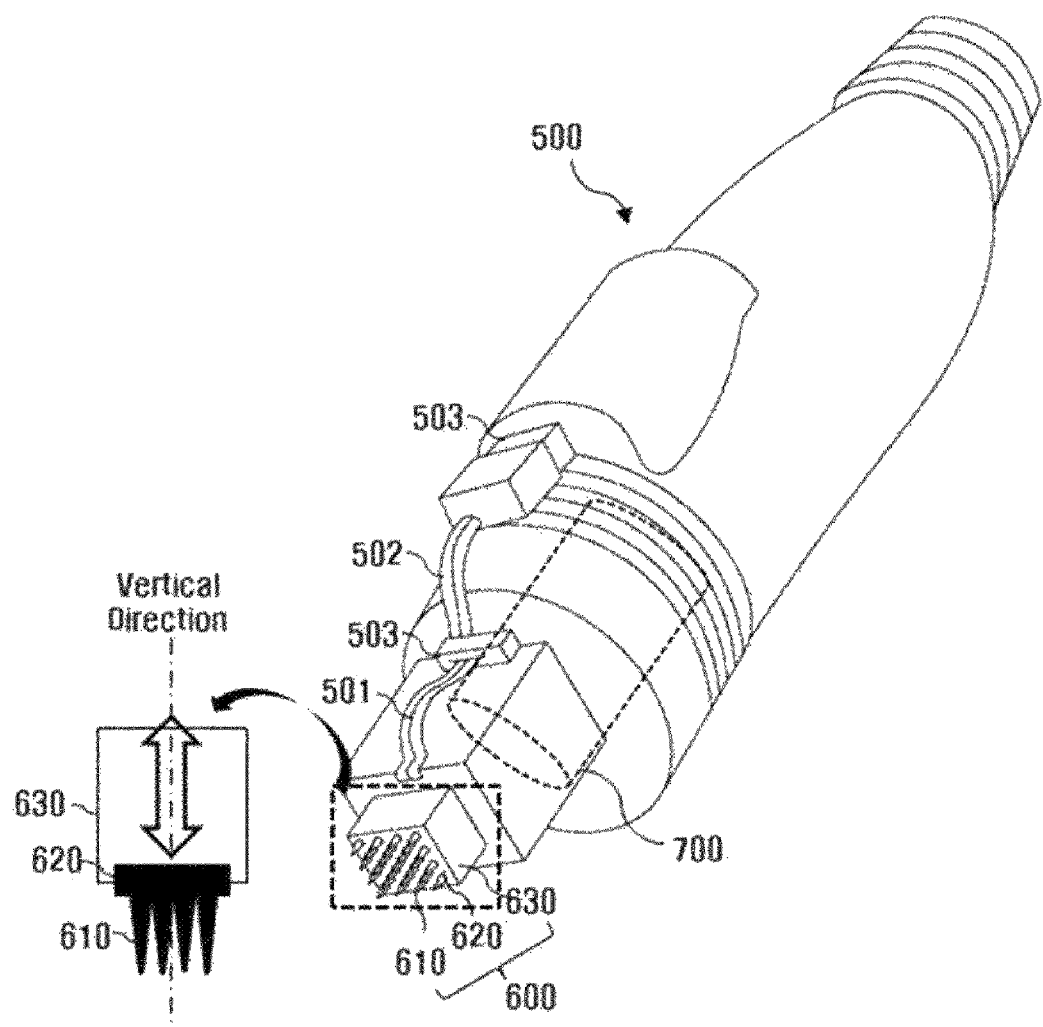
FIG. 5 is a perspective view illustrating a needle tip mounted on a skin scare device according to the inventive concept.
Figure 6:
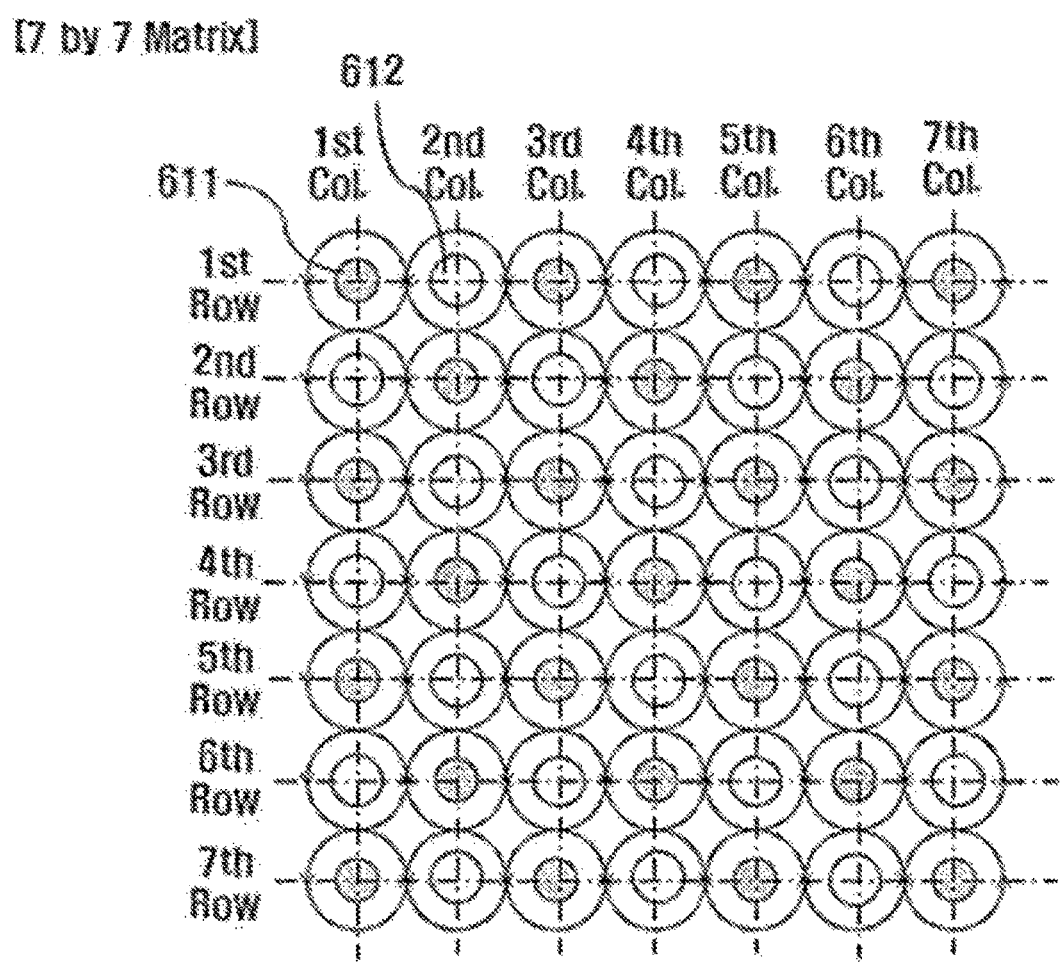
FIG. 6 is a plan view illustrating a needle tip mounted on a skin care device according to the inventive concept.

Hereinafter, a skin care device 1000 will be described with reference to accompanying drawings according to the inventive concept. FIG. 4 is a schematic view illustrating a skin care device according to the inventive concept, FIG. 5 is a perspective view illustrating a needle tip mounted on a skin scare device according to the inventive concept, FIG. 6 is a plan view illustrating a needle tip mounted on a skin care device according to the inventive concept, and FIGS. 7A and 7B is a plan view illustrating that a first group of needle electrodes and a second group of needle electrodes are divided, according to the inventive concept.

Hereinafter, a skin care device 1000 according to the inventive concept will be described with reference to accompanying drawings. FIG. 4 is a schematic view illustrating the skin care device according to the inventive concept, FIG. 5 is a perspective view illustrating a needle tip mounted on the skin care device, according to the inventive concept, FIG. 6 is a plan view illustrating the needle tip mounted on the skin care device according to the inventive concept, and FIGS. 7A and 7B plan views separately illustrating a first group of a plurality of needle electrodes and a second group of a plurality of needle electrodes according to the inventive concept.

Hereinafter, the term "vertical direction" may be a vertical direction illustrated in FIG. 5, and may be used interchangeably with the term "up-and-down direction". One side in the "vertical direction" may be an upper portion, and another side in the "vertical direction" may be a lower portion.

According to the inventive concept, a skin care device 1000 may include a main body 100, a display module 200, an operating module 300, an electronic control module (not illustrated), a conductive module 400, a hand piece 500, a needle tip 600, a driving module 700, and a ground electrode pad 800. The main body 100 may include the display module 200 and the operating module 300. The display module 200 may be manufactured in the form of a panel to visually provide various piece of information to a doctor instructing a skin care procedure. For example, the display module 200 may display, in the form of a graph, the output level or an impedance of the high frequency applied to a dermal layer of a present target point. In addition, the display module 200 may display an operating mode currently being performed by the skin care device 1000 according to the inventive concept. In addition, the display module 200 may display biometric information of a deep portion of the skin tissue at the target point.

The operating module 300 may be provided in the form of a button on the outer surface of the main body 100. The doctor may turn on/off the skin care device 1000 through the operating module 300, select an operating mode of the skin care device 1000, and change an output level of the high frequency applied to a target point.

Meanwhile, when the display module 200 is provided in the form of a touch screen, at least a portion of the operating module 300 may be omitted. In this case, the doctor may operate the skin care device 1000 by touching a menu displayed on the screen of the display module 200.

An electronic control module (not illustrated) may be embedded in the main body 100 to electronically control components of the skin care device 1000. To this end, the electronic control module may be electrically connected with the needle tip 600, the driving module 700, and the ground electrode pad 800 through the conductive module 400. In other words, the electronic control module may apply a current and an electronic control signal, which corresponds to an operating signal applied by a doctor, to the needle tip 600 and the driving module 700, in response to the operation signal by the doctor.

For example, a wavelength, an intensity, and a direction of a current applied to the plurality of needle electrodes 610 of the needle tip 600 may be controlled through the control signal of the electronic control module, and a current may be selectively applied to a first group 611 of a plurality of needle electrodes 610 and a second group 612 of a plurality of needle electrode 610 of the needle tip 600 through the control signal of the electrode control module.

Furthermore, according to the inventive concept, the electronic control module may apply a current to the first group 611 of the plurality of needle electrodes 610 and the second group 612 of the plurality of needle electrodes 610 at different times. In other words, a current may be applied to the plurality of needle electrodes 610 in such a manner that the current is alternately applied to the first group 611 of the plurality of needle electrodes 610 and the second group 612 of the plurality of needle electrodes 610 (alternating oscillation of high frequency).

In addition, a driving period of the driving module 700 may be controlled through a control signal of the electronic control module. Accordingly, the reciprocating driving period of the plurality of needle electrodes 610 of the needle tip 600 may be controlled based on a vertical direction of the holder 620. Meanwhile, the current applied to the plurality of needle electrodes 610 of the needle tip 600 may be refluxed from the ground electrode pad 800.

In addition, the output level of the power module may be controlled through the electronic control signal of the electronic control module. Therefore, the wavelength, direction, and intensity of a current applied to the plurality of needle electrodes 610 of a needle unit of the needle tip 600 may be changed, and thus the output level of the high frequency applied to the target point may be controlled.

The conductive module 400 may electrically connect the electronic control module with the needle tip 600, may electrically connect the electronic control module with the driving module 700, and the electronic control module with the ground electrode pad 800. In other words, the conductive module 400 may form a conductive line of the skin care device 1000 of the inventive concept.

The conductive module 400 may extend to one side in the main body 100. Meanwhile, the conductive module 400 may electrically connect the electronic control module and the needle tip 600, and may include a first cable 410 to electrically connect the electronic control module with the driving module 700. In addition, the conductive module 400 may include a second cable 420 to electrically connect the electronic control module with the ground electrode pad 800.

Therefore, the current applied from the electronic control module is applied to the plurality of needle electrodes 610 of the needle tip 600 through the first cable 410, and the ground electrode pad 800 is electrically connected with the electronic control module through the second cable 420 to allow the current, which is applied to the plurality of needle electrodes 610 of the needle tip 600 to reflux (mono-polar method). Therefore, a high frequency may be generated in the deep portion of the skin at the target point, thereby dissipating heat energy.

A plurality of wires may be provided in the first cable 410 and the second cable 420 to form respective channels depending on types of a current and an electronic control signal, and an outer skin of the first cable 410 and the second cable 420 may insulate and cover a bundle of wires having various channels.

The hand piece 500 is a part held by the doctor. In addition, the doctor may change the target point (e.g., a part of the face) by moving the hand piece 500 in contact with the skin of a target person. The hand piece 500 may be disposed on the first cable 410 of the conductive module 400 and may be positioned at an end portion of the first cable 410 of the conductive module 400 in the extending direction of the first cable 410.

The hand piece 500 may has the driving module 700 provided therein, and the end of the hand piece 500 may be equipped with a needle tip 600. Therefore, the first cable 410 of the conductive module 400 allows the driving module 700 provided in the hand piece 500 and the plurality of needle electrodes 610 of the needle tip 600 mounted on the hand piece 500 to be electrically connected with the electronic control module.

The hand piece 500 may be provided at the outer portion thereof with a first conductive member 501, a second conductive member 502, and a cable connector 503 to electrically connect the plurality of needle electrodes 610 of the needle tip 600 with the first cable 410 of the conductive module 400.

In this case, the first conductive member 501 and the second conductive member 502 may be manufactured in the form of a film. For example, the first conductive member 501 and the second conductive member 502 may be flexible printed circuit boards (FPCBs). The plurality of needle electrodes 610 and the holder 620 of the needle tip 600 reciprocate (drive) in the vertical direction. Accordingly, the first and second conductive members 501 and 502 of the hand piece 500 are provided at the outer portion of the hand piece 500 to prevent the first and second conductive members 501 and 502 of the hand piece 500 from interrupting the reciprocation of the plurality of needle electrodes 610 of the needle tip 600 and the holder 620 of the needle tip 600 during the reciprocation of the plurality of needle electrodes 610 of the needle tip 600 and the holder 620 of the needle tip 600.

The needle tip 600 may be a member to apply a high frequency to the deep portion of the skin at the target point.

The needle tip 600 may be detachably mounted to an end of hand piece 500. In other words, the needle tip 600 of the inventive concept may be manufactured in the form of a cartridge and thus may be replaceable with new one.

The needle tip 600 may include the plurality of needle electrodes 610, the holder 620, and a case 630. The plurality of needle electrodes 610 of the needle tip 600 and the holder 620 of the needle tip 600, which serve as "actuators", the needle electrode 610 of the needle tip 600 is invaded into the deep portion of the skin of the target point with a specific period (driving period of the driving module) to apply the high frequency to the dermal layer of the skin. The holder 620 of the needle tip 600 may be a member to fix and support the plurality of needle electrodes 610 of the needle tip 600. The case 630 of the needle tip 600, which serves as a stator, may be a member detachably mounted to the end of the hand piece 500.

The plurality of needle electrodes 610 may be electrically connected with the electronic control module through the first cable 410 of the conductive module 400 to receive a current, and the current applied to the plurality of needle electrodes 610 may be refluxed to the ground electrode pad 800. In this process, high frequency may be generated in the deep portion of the skin at the target point.

Meanwhile, as described above, the plurality of needle electrodes 610 may be electrically connected with the power module through the first conductive member 501 of the hand piece 500, the second conductive member 502 of the hand piece 500, and the cable connector 503 of the hand piece 500. The cable connector 503 may be electrically connected with the power module.

The plurality of needle electrodes 610 may be fixed to the holder 620 and may extend downward from the holder 620. The plurality of needle electrodes 610 may reciprocate in the vertical direction together with the holder 620 by the driving force of the driving module 700. In this case, the lower end portions of the plurality of needle electrodes 610 at the bottom dead center may be disposed on the deep portion of the skin at the target point, and the lower end portions of the plurality of needle electrodes 610 at the top dead center may be disposed on the surface of the skin at the target point. In other words, the plurality of needle electrodes 610 may be repeatedly (periodically) invaded the deep portion of the skin at the target point.

The plurality of needle electrodes 610 may be a monopolar type electrode unit in which all the plurality of electrodes have the same polarity. In other words, the current applied to the plurality of needle electrodes 610 may be refluxed in the ground electrode pad 800 provided separately. An alternating current may be applied to the plurality of needle electrodes 610.

Figure 1B:
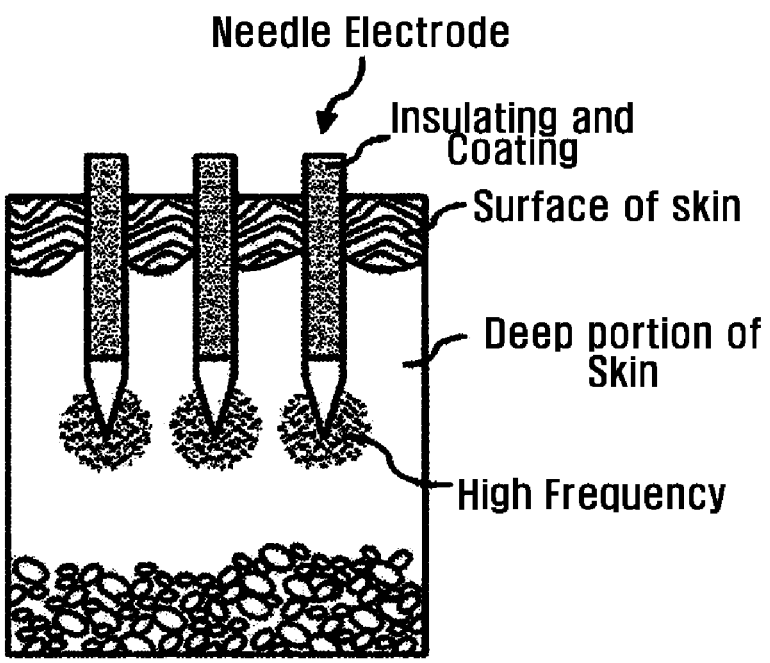
Figure 2:
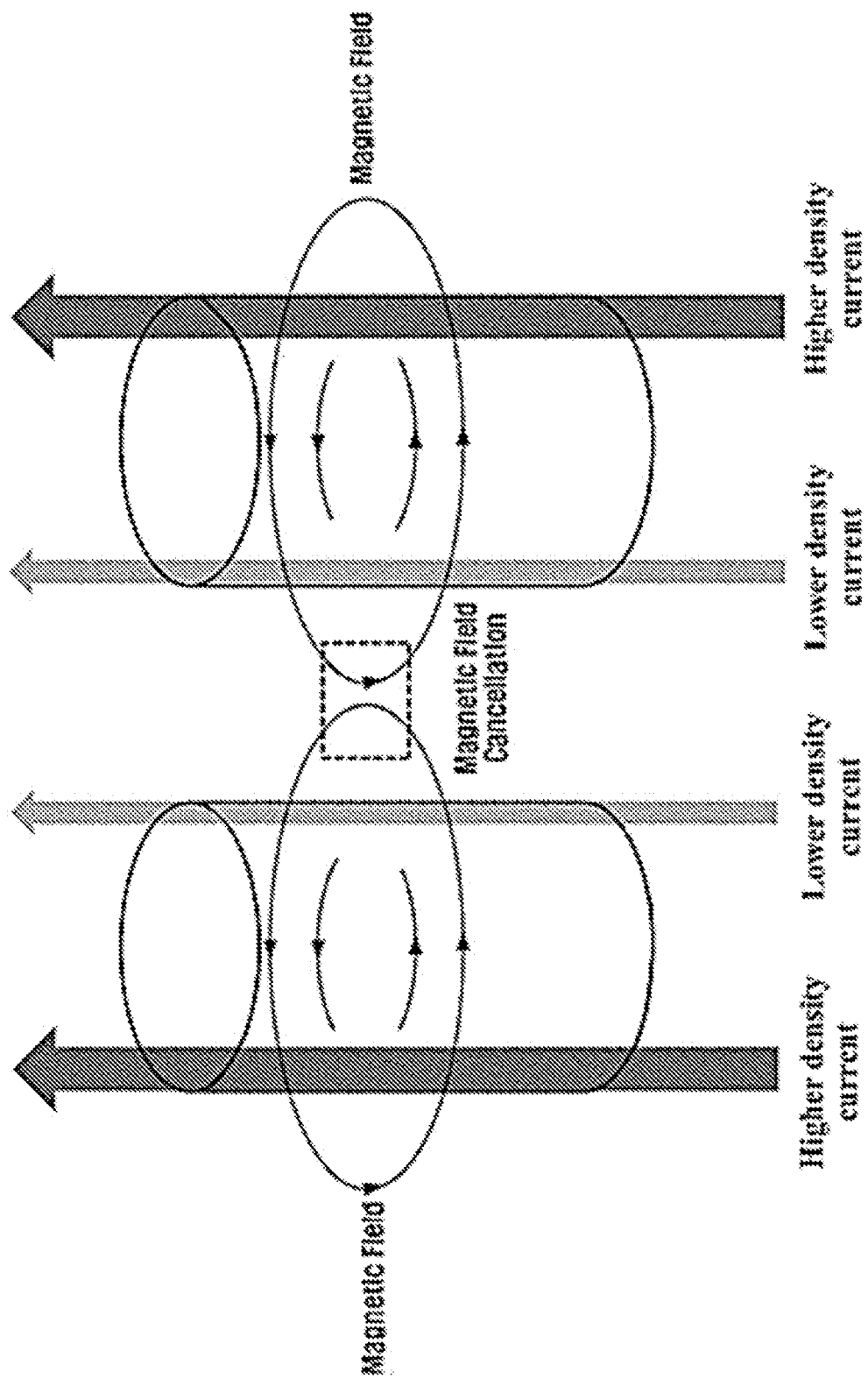
FIG. 2 is a schematic view illustrating that a current flows while being deflected as a magnetic field is cancelled between mutually adjacent needle electrodes.
Figure 3:
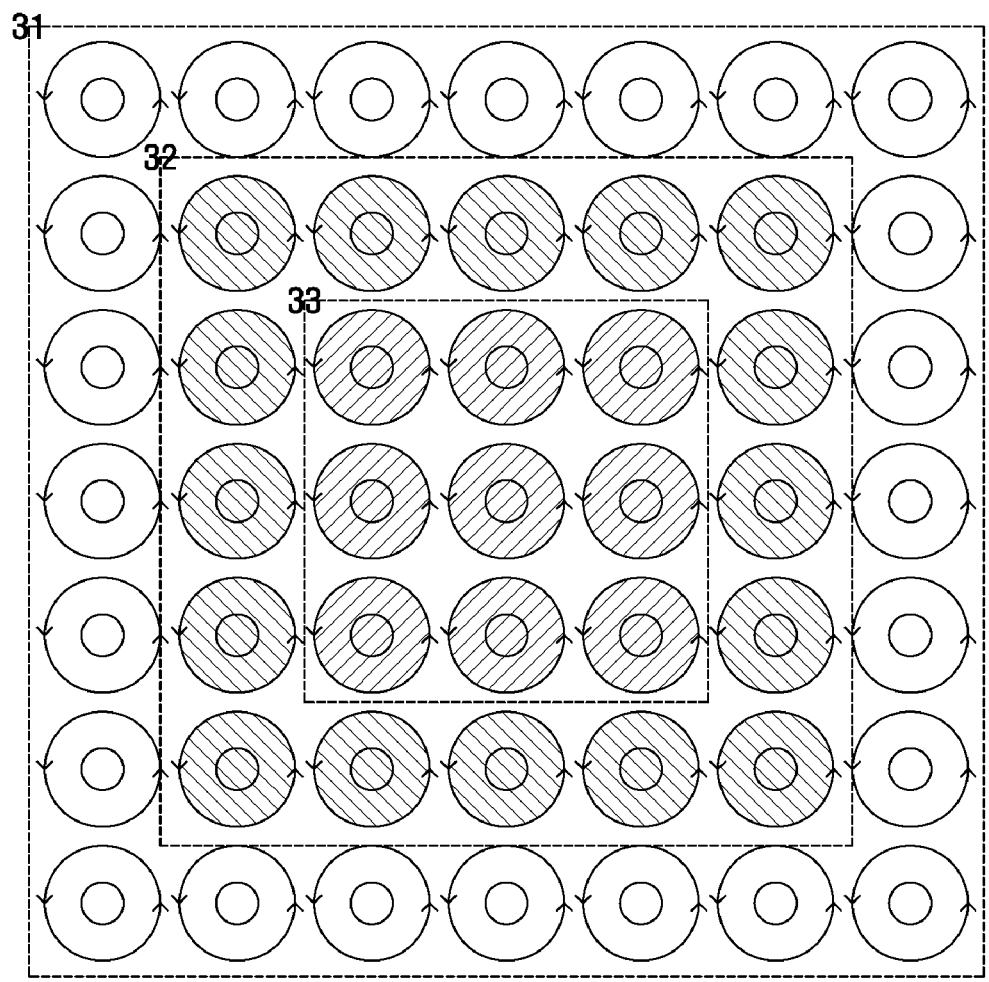
FIG. 3 is a schematic view illustrating that a proximity effect occurs between a plurality of needle electrodes arranged in the form of a matrix.

Tip ends may be formed at the lower ends of the plurality of needle electrodes 610. The plurality of needle electrodes 610 may be insulated and coated except for the tips thereof and the adjacent portions of the tip ends. In this case, high frequency is generated only at the tip ends of the plurality of needle electrodes 610 and the adjacent portions of the tips, so thermal energy may be intensively generated only at a specific deep portion at the target point (see FIG. 1B).

The plurality of needle electrodes 610 may include a first group 611 of needle electrodes and a second group 612 of needle electrodes to which a current is applied at different times. In other words, according to the inventive concept, the plurality of needle electrodes 610 in the needle tip 600 may be divided into two or more groups, and a current may be alternately applied to the two or more groups (alternating oscillation).

To this end, although various circuit configurations are possible, it is preferred that the first group 611 of the plurality of needle electrodes 610 and the second group 612 of the plurality of needle electrodes 610 are connected with the same power source (electronic control module) in parallel, and the switch is operated such that the power is alternately applied to the first group 611 of the plurality of needle electrodes 610 and the second group 612 of the plurality of needle electrodes 610.

According to the skin care device 1000 of the inventive concept, the proximity effect occurring between the adjacent needle electrodes may be prevented due to the alternating oscillation (the groups are alternately oscillated).

Meanwhile, to effectively prevent the proximity effect, the first group 611 of the plurality of needle electrodes 610 and the second group 612 of the plurality of needle electrodes 610 have to be spaced apart from each other as far as possible on a plane having a limited area.

The following description will be made, with reference to FIGS. 6 and 7, regarding the manner of arranging the first group 611 of the plurality of needle electrodes 610 and the second group 612 of the plurality of needle electrodes 610 to effectively prevent the proximity effect.

The plurality of needle electrodes 610 may be arranged to have one or more rows and one or more columns on a plane perpendicular to the vertical direction. In other words, according to the inventive concept, the plurality of needle electrodes 610 of the needle tip 600 may be preferably arranged in a matrix form, but is not limited thereto, and may be arranged in one row or in one column.

In this case, the first group 611 of the plurality of needle electrodes 610 and the second group 612 of the plurality of needle electrodes 610 may be arranged alternately based on one or more columns, and alternately arranged based on one or more rows. Furthermore, the first group 611 of the plurality of needle electrodes 610 may be arranged on a plane perpendicular to the vertical direction in one or more first diagonal lines which may be inclined with respect to one or more rows or columns and parallel to each other. Furthermore, the second group 612 of the plurality of needle electrodes 610 may be arranged on a plane perpendicular to the vertical direction in one or more second diagonal lines which may be inclined with respect to one or more rows or columns and parallel to each other. One or more first diagonals and one or more second diagonals may be parallel to each other (the inclination angles formed between the first diagonal line and the second diagonal line, and one or more columns and one or more rows are 45 degrees).

Therefore, on the assumption that the distance between adjacent needle electrodes in one or more rows and one or more columns is "a", the shortest distance between one needle electrode of the first group 611 and one needle electrode of the second group of 612, which are close to each other, may be "$\sqrt{2}*a$", and the maximum distance may be "2a" (the distance between the electrode in the first group and the electrode in the second group is ensured).

Accordingly, a plurality of needle electrodes are arranged at an appropriate density on a plane having a limited target point and the distance between needle electrodes close to each other is ensured, thereby preventing the proximity effect.

Meanwhile, according to the inventive concept, as the plurality of needle electrode 610 of the needle tip 600 may be arranged such that the total 49 electrodes are arranged while forming 7 columns and 7 rows by performing trade-off between the output level of high-frequency energy per a unit volume, which is applied to the deep portion of the skin at the target point, and the output level of electric energy per a unit electrode, which is applied to the electronic control module. In this case, 7 electrodes may be arranged in a unit row and 7 electrodes may be arranged in a unit column.

It should be noted that the plurality of needle electrodes 610 according to the inventive concept are not arranged in a typical matrix form (a plurality of needle electrodes are all filled in the grid points of rows and columns at equal spacings). In other words, it should be noted that the scope of the right of the needle tip 600 and the skin care device 1000 of the inventive concept covers the case in which the plurality of needle electrodes 610 are arranged in an atypical matrix form. For example, in a plurality of needle electrodes arranged in the form of a matrix having seven rows and seven columns (7 by 7 Matrix), based on the request of electromagnetic design conditions and mechanical design conditions, an electrode in the first row and the first column ($1^{st}$ ROW and $1^{st}$ Col.), an electrode in the first row and the seventh column ($1^{st}$ ROW, and $7^{th}$ Col.), and an electrode in the seventh row and the first column ($7^{th}$ ROW, and $1^{st}$ Col.) and an electrode in the seventh row and the seventh row ($7^{th}$ ROW, $7^{th}$ Col.) may be omitted, and to the contrary, a plurality of electrodes are added to have another matrix form other than a typical matrix form (a 7 by 7 matrix).

The case 630 may be hollowed in the vertical direction. The plurality of needle electrodes 610 and the holder 620 may be disposed in the inner space of the case 630. The bottom surface of the case 630 may be opened, and the lower end of the case 630 may be disposed on the surface of the skin at the target point.

In this case, the lower portion of the case 630 may have an inner space formed by the holder 620, the sidewall of the case 630, and the surface of the skin of the target point. The plurality of needle electrodes 610 may invade the skin at the target point by passing through the open lower portion of the case 630.

The volume of the inner space of the case 630 may vary with the position of the holder 620 in the vertical direction. In other words, the volume of the inner space of the case 630 may have a maximum value at the top dead center of the holder 620 and may have a minimum value at the bottom dead center of the holder 620.

The driving module 700 may be embedded in the hand piece 500 and may provide driving force to allow the plurality of needle electrodes 610 and the holder 620 of the needle tip 600 to reciprocate. Various types of driving devices may be used as the driving device of the driving module 700. For example, the driving module 700 may include a pneumatic cylinder or may include a linear motor.

The ground electrode pad 800 may be disposed at an end portion of the second cable 420 of the conductive module 400. The ground electrode pad 800 may be electrically connected with the electronic control module and may reflux the current applied to one or more needle electrodes 610 of the needle tip 600. The ground electrode pad 800 may be disposed at any point other than the target point during the procedure. In other words, the ground electrode pad 800 may be disposed on the skin surface of the back or the valley of the target person during the procedure.

The inventive concept provides a needle tip mounted on a skin care device in a monopolar type, in which a plurality of needle electrodes are divided into a first group and a second group and a current is alternately applied to the first group and the second group (alternating oscillation; a frequency is alternately oscillated in the first group and the second group).

Further, according to the inventive concept, the first group of needle electrodes and the second group of the needle electrodes are alternately arranged in the form of a matrix and mutually alternately arranged along a row and a column, so the first group of needle electrodes and the second group of needle electrodes are spaced apart from each other as much as possible, on a limited plane.

Therefore, the inventive concept provides a needle tip, in which a proper high frequency energy may be ensured within a reference area of the surface of the skin at the target point while a plurality of needle electrodes are alternately oscillated, thereby preventing the proximity effect, and a skin care device equipped with the needle tip.

The effects of the inventive concept are not limited to the above, but other effects, which are not mentioned, will be apparently understood to those skilled in the art.

Although embodiments of the inventive concept have been described with reference to accompanying drawings, those skilled in the art should understand that various modifications are possible without departing from the technical scope of the inventive concept or without changing the subject matter of the inventive concept. Therefore, those skilled in the art should understand that the technical embodiments are provided for the illustrative purpose in all aspects and the inventive concept is not limited thereto.

What is claimed is:

1. A needle tip for a skin care device, the needle tip comprising:
   a holder; and
   a plurality of needle electrodes disposed in the holder;
   wherein the plurality of needle electrodes is arranged in a grid having one or more rows and one or more columns, wherein the plurality of needle electrodes includes a first group of needle electrodes and a second group of needle electrodes, and wherein each needle electrode of the first group of needle electrodes is not row-wise or column-wise adjacent to any needle electrode of the second group of needle electrodes, and wherein each needle electrode of the second group of needle electrodes is not row-wise or column-wise adjacent to any needle electrode of the first group of needle electrodes; and
   wherein the first group of needle electrodes and the second group of needle electrodes are electrically connected in parallel to one another such that the first group of needle electrodes and the second group of needle electrodes are configured for monopolar operation whereby energy is applied to skin through the first group of needle electrodes and the second group of needle electrodes, respectively, at mutually different times, and whereby the first group of needle electrodes and the second group of needle electrodes have the same polarity.

2. The needle tip of claim 1, wherein the plurality of needle electrodes is on a plane perpendicular to a direction corresponding to reciprocation of the holder.

3. The needle tip of claim 2, wherein the needle electrodes of the first group are arranged along one or more first diagonal lines on the plane;
   wherein the needle electrodes of the second group are arranged along one or more second diagonal lines on the plane; and
   wherein the one or more first diagonal lines and the one or more second diagonal lines are not overlapping and are parallel to each other.

4. The needle tip of claim 3, wherein each of the one or more first diagonal lines and the one or more second diagonal lines is aligned at a 45 degree angle with respect to each of the one or more rows and the one or more columns, on the plane.

5. The needle tip of claim 4, wherein a number of the plurality of needle electrodes is 49, a number of the one or more rows is seven, and a number of the one or more columns is seven.

6. The needle tip of claim 1, further comprising:
   a switch configured to switch between energy being supplied to the first group of needle electrodes and energy being supplied to the second group of needle electrodes.

7. A skin care device comprising:
   a main body in which a user interface is disposed;
   a connector extending to one side of the main body and including a first cable and a second cable;
   a hand piece disposed on the first cable;
   a needle tip mounted on the hand piece;
   a driving device;
   a ground electrode pad disposed on the second cable; and
   a controller electrically connected with the needle tip through the first cable and electrically connected with the ground electrode pad through the second cable;
   wherein the needle tip includes:
      a case;
      a holder disposed in the case to reciprocate in a vertical direction by the driving device; and
      a plurality of needle electrodes disposed in the holder; and
   wherein the plurality of needle electrodes includes a first group of needle electrodes and a second group of needle electrodes; and
   wherein the controller is configured to apply a current to the first group of needle electrodes and the second group of needle electrodes, respectively, at mutually different times.

8. The device of claim 7, wherein the plurality of needle electrodes is on a plane perpendicular to a direction corresponding to reciprocation of the holder.

9. The device of claim 8, wherein the needle electrodes of the first group are arranged along one or more first diagonal lines on the plane;
   wherein the needle electrodes of the second group are arranged along one or more second diagonal lines on the plane; and
   wherein the one or more first diagonal lines and the one or more second diagonal lines are not overlapping and are parallel to each other.

10. The device of claim 9, wherein each of the one or more first diagonal lines and the one or more second diagonal lines is aligned at a 45 degree angle with respect to each of the one or more rows and the one or more columns, on the plane.

11. The device of claim 10, wherein a number of the plurality of needle electrodes is 49, a number of the one or more rows is seven, and a number of the one or more columns is seven.

12. The device of claim 7, wherein the main body includes a power source configured to supply energy to the first and second groups of needle electrodes.

13. The device of claim 12, further comprising:
   a switch configured to switch between energy from the power source being supplied to the first group of needle electrodes and energy from the power source being supplied to the second group of needle electrodes.

14. A skin care device, comprising:
   a hand piece; and a needle tip configured to be mounted on the hand piece;

wherein the needle tip includes a plurality of needle electrodes;

wherein the plurality of needle electrodes is arranged in a grid having one or more rows and one or more columns, wherein the plurality of needle electrodes includes a first group of needle electrodes and a second group of needle electrodes, and wherein each needle electrode of the first group of needle electrodes is not row-wise or column-wise adjacent to any needle electrode of the second group of needle electrodes, and wherein each needle electrode of the second group of needle electrodes is not row-wise or column-wise adjacent to any needle electrode of the first group of needle electrodes; and wherein the first group of needle electrodes and the second group of needle electrodes are electrically connected in parallel to one another such that the first group of needle electrodes and the second group of needle electrodes are configured for monopolar operation whereby energy is applied to skin through the first group of needle electrodes and the second group of needle electrodes, respectively, at mutually different times, and whereby the first group of needle electrodes and the second group of needle electrodes have the same polarity.

15. The device of claim 14, wherein the plurality of needle electrodes is on a plane perpendicular to a direction corresponding to reciprocation of the holder.

16. The device of claim 15, wherein the needle electrodes of the first group are arranged along one or more first diagonal lines on the plane;

wherein the needle electrodes of the second group are arranged along one or more second diagonal lines on the plane; and wherein the one or more first diagonal lines and the one or more second diagonal lines are not overlapping and are parallel to each other.

17. The device of claim 16, wherein each of the one or more first diagonal lines and the one or more second diagonal lines is aligned at a 45 degree angle with respect to each of the one or more rows and the one or more columns, on the plane.

18. The device of claim 17, wherein a number of the plurality of needle electrodes is 49, a number of the one or more rows is seven, and a number of the one or more columns is seven.

19. The device of claim 14, further comprising:

a switch configured to switch between energy from the power source being supplied to the first group of needle electrodes and energy from the power source being supplied to the second group of needle electrodes.

* * * * *